United States Patent
Burke

Patent Number: 5,507,831
Date of Patent: Apr. 16, 1996

[54] DISTAL STEM CENTRALIZER FOR FEMORAL PROSTHESIS

[76] Inventor: Dennis W. Burke, 245 Highland St., Milton, Mass. 02186

[21] Appl. No.: 176,665

[22] Filed: Jan. 3, 1994

[51] Int. Cl.⁶ ..................................................... A61F 2/36
[52] U.S. Cl. .................................. 623/23; 623/16; 606/95
[58] Field of Search ............................. 623/16, 22, 23, 623/18; 606/60–62, 95

[56] References Cited

U.S. PATENT DOCUMENTS

| | | |
|---|---|---|
| D. 339,865 | 9/1993 | Geremakis et al. . |
| 3,793,650 | 2/1974 | Ling et al. . |
| 4,268,920 | 5/1981 | Engelbrecht et al. . |
| 4,623,353 | 11/1986 | Buechel et al. ............................. 623/23 |
| 5,078,746 | 1/1992 | Garner ........................................ 623/16 |
| 5,080,680 | 1/1992 | Mikhail et al. ............................. 623/16 |
| 5,108,439 | 4/1992 | Morscher et al. . |

FOREIGN PATENT DOCUMENTS 2104391 of 0000 United Kingdom .
1409053 10/1975 United Kingdom ..................... 623/22

OTHER PUBLICATIONS

Richards—Modular Hip System—No date available.
Zimmer—Harris Precoat Plus Hip Prosthesis—1988.

*Primary Examiner*—Randall L. Green
*Assistant Examiner*—Rob Clarke
*Attorney, Agent, or Firm*—H. Jay Spiegel

[57] ABSTRACT

A centralizer is installed on the end of the distal stem of a femoral prosthesis by virtue of splines cut into the sides of the tip of the distal end of the stem. Each spline has a relatively shallow distal portion and a deeper proximal portion. The centralizer has legs, each one of which has a radially inwardly directed surface designed to enter a respective spline. The proximal end of each leg of the centralizer is thicker in a radial direction including a radially inwardly directed projection entering the proximal portion of the spline to lock the centralizer in mounted position on the distal end of the stem. The centralizer acts to center the distal stem of the femoral prosthesis within the intramedullary canal of the proximal femur.

12 Claims, 2 Drawing Sheets

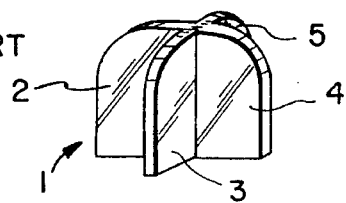
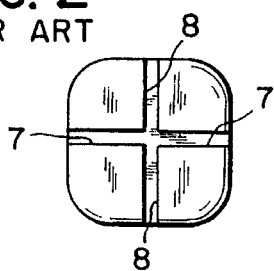
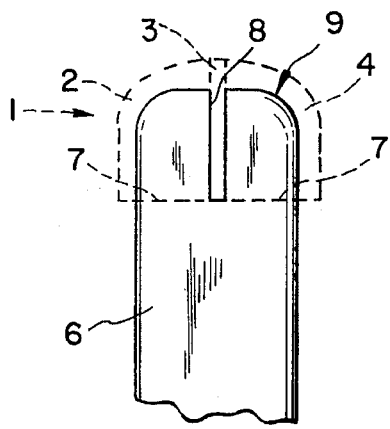
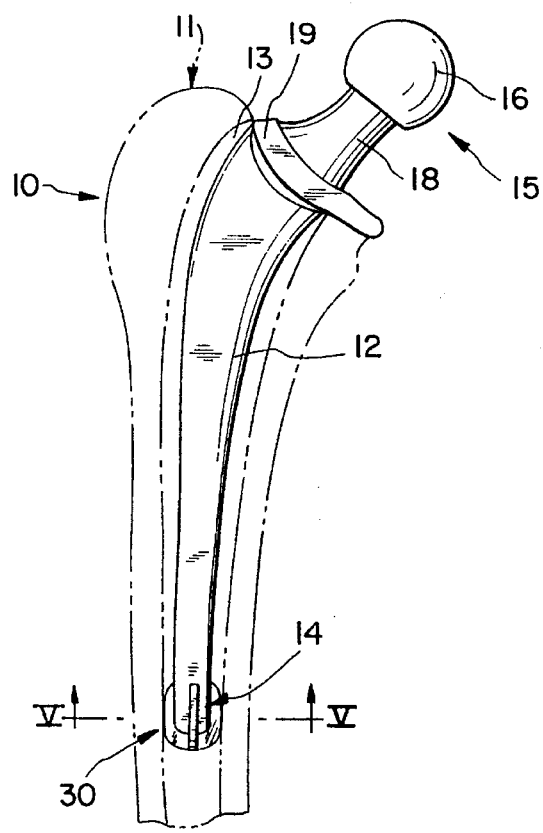
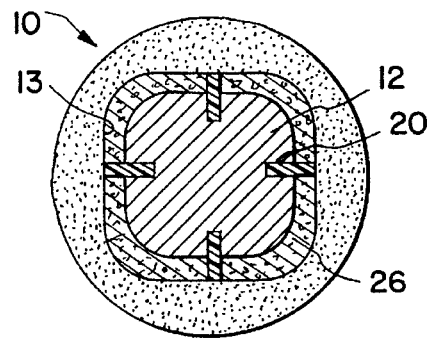

DISTAL STEM CENTRALIZER FOR FEMORAL PROSTHESIS

BACKGROUND OF THE INVENTION

The present invention relates to a distal stem centralizer for femoral prosthesis. In the prior art, centralizer mechanisms are known. However, Applicant is unaware of any such device including all of the features and aspects of the present invention.

ORTHOMET manufactures a femoral prosthesis including a centralizer mechanism having a stem which fits within a hole formed in the distal stem tip. The centralizer extends distally of the stem including blade-like appendages extending radially outwardly and into engagement with the intramedullary canal. This design has proven unreliable, in practice, in that, occasionally, the finned portion of the centralizer may break away from the stem portion which is received within the hole formed within the distal stem. Furthermore, the shape of the fins of this centralizer creates turbulence in the cement which is inserted within the intramedullary canal and through which the centralizer and distal stem of the femoral prosthesis travel as they are inserted within the intramedullary canal and through the cement to their location of final installation. Additionally, proximal movements of the distal stem during installation can dislodge this centralizer from the distal stem tip.

RICHARDS has developed a centralizer which will be described in greater detail with reference to FIGS. 1–3 herein. In using the RICHARDS centralizer, two mutually perpendicular slots are cut through the end of the distal stem and the RICHARDS centralizer which includes two crossed diametrical fins is inserted within the slots cut through the stem. The slots create four sharp corners as well as four thin stem tip portions which may weaken the distal stem and are difficult to create. Furthermore, this centralizer does not include any locking mechanism which would preclude accidental removal during installation. For example, if the surgeon is inserting a femoral prosthesis within the intramedullary canal of the proximal femur and, during insertion, must slightly pull the femoral prosthesis in the proximal direction, it is possible that this centralizer could be inadvertently removed and lost within the cement within the intramedullary canal, thus requiring complete removal of the cement as well as the centralizer and re-insertion of cement and installation of a new centralizer, thereby extending surgery time.

As such, a need has developed for a femoral prosthesis distal stem centralizer which is easy to install, requires only slight modification of the distal stem and which reliably locks in installed position. It is with these aspects in mind that the present invention was developed.

SUMMARY OF THE INVENTION

The present invention relates to a distal stem centralizer for femoral prosthesis. The present invention includes the following interrelated objects, aspects and features:

(A) In a first aspect, in order to install the inventive centralizer, the distal stem of the femoral prosthesis is modified through machining of four splines in the side walls of the tip thereof. In the preferred embodiment, the splines are orthogonal to adjacent splines and are easily machined through the use, for example, of a carbide slitting saw. The splines define an internal geometry at the stem tip and have proximal portions which are deeper than the distal portions thereof to provide a self-locking mechanism for the centralizer which is to be received therein.

(B) The centralizer has a distal tip and four proximally directed legs extending arcuately from the distal tip. Each leg includes a proximal portion which is thicker, radially, than the distal portion thereof with these radially thicker proximal portions being designed to enter into the deeper proximal portions of the splines to lock the centralizer in mounted position. Each spline has an outer surface extending radially outwardly from the dimensions of the stem tip so that the centralizer is operative to center the stem within the intramedullary canal of the proximal femur as opposed to the prior art which centralizes distal of the stem tip (the ORTHOMET centralizer) or, in some cases, proximal to the tip.

(C) In a further aspect, the area of the centralizer of the present invention which extends radially outwardly from the stem tip is made of an extremely low area profile with the legs thereof extending parallel to the axis of insertion of the prosthesis within the intramedullary canal of the proximal femur. This design results in minimal turbulent flow of cement during insertion. In the preferred embodiment of the present invention, the inventive centralizer is made of an acrylic plastic.

As such, it is a first object of the present invention to provide a distal stem centralizer for femoral prosthesis.

It is a further object of the present invention to provide such a centralizer with legs designed to fit into splines formed in the tip of the distal stem of a femoral prosthesis.

It is a still further object of the present invention to provide such a centralizer with legs having thickened proximal ends designed to lock into deeper proximal portions of the respective splines.

It is a still further object of the present invention to provide such a centralizer made of an acrylic plastic.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a perspective view of a prior art centralizer device.

FIG. 2 shows a view looking proximally at the tip of the distal stem of a femoral prosthesis modified to receive the centralizer illustrated in FIG. 1.

FIG. 3 shows a side view of the tip of the distal stem shown in FIG. 2.

FIG. 4 shows a side view of a femoral prosthesis having the present invention installed on the distal stem tip thereof and inserted within the intramedullary canal of a proximal femur with the proximal femur and intramedullary canal shown in cross-section.

FIG. 5 shows a cross-sectional view along the line V—V of FIG. 4.

SPECIFIC DESCRIPTION OF THE PREFERRED EMBODIMENT

Figure 6:
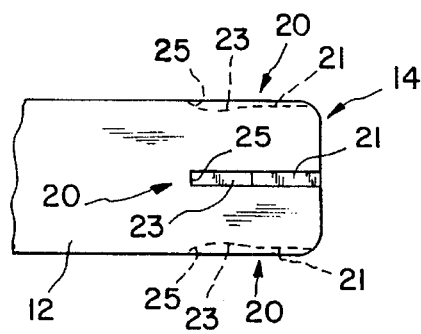
FIG. 6 shows a side view of the tip of the distal stem of a femoral prosthesis.

Reference is first made to FIGS. 1–3 so that a description of a prior art centralizer may be described. FIG. 1 shows the centralizer 1 having radially outwardly extending legs 2, 3, 4 and 5.

FIGS. 2 and 3 show the tip of the distal stem of a femoral prosthesis with the tip being generally designated by the reference numeral 9. As seen in FIGS. 2 and 3, perpendicular slots 7 and 8 are cut into the tip 9 to receive the legs 2, 3, 4 and 5 of the centralizer 1. The manner of installation of the centralizer 1 on the tip 9 of the stem 6 of the femoral prosthesis should be understood from viewing FIGS. 1–3. The cross-shape of the slots 7 and 8 is best seen in FIG. 2 and the corresponding cross-shape of the centralizer 1 allows receipt within the slots 7 and 8 as shown in phantom in FIG. 3. As seen, in particular, in FIGS. 2 and 3, the width of the slots 7 and 8 is uniform top-to-bottom, thus, no locking mechanism exists to retain the centralizer 1 in mounted position as shown in FIG. 3. Furthermore, as explained above, it is expensive to machine the slots 7 and 8 in the tip 9 of the stem 6 of the femoral prosthesis. Additionally, the slots 7, 8 inherently weaken the tip 9.

With reference, now, to FIGS. 4–10, the present invention will be explained in great detail.

As shown in FIG. 4, the proximal femur is generally designated by the reference numeral 10 and includes a proximal end 11 as well as an intramedullary canal 13 which is normally filled with marrow. A femoral prosthesis is generally designated by the reference numeral 15 and includes a head 16, a neck 18, a collar 19 and a distal stem 12 having a tip 14. In installing a femoral prosthesis 15 in the proximal femur 10, within the intramedullary canal 13, marrow is removed from the intramedullary canal 13 and it is replaced with a cement 26 (FIG. 5). The femoral prosthesis 15 is then inserted within the intramedullary canal 13 to the position shown in FIG. 4.

The inventive centralizer 30 is seen, in FIGS. 4 and 5, to space the outer walls of the distal stem 12 and the tip 14 of the prosthesis 15 from the walls of the intramedullary canal 13. As is known by those skilled in the art, it is desirable to have the prosthesis located centrally within the intramedullary canal 13 so that a uniform layer of acrylic cement surrounds the distal stem 12 and tip 14. It has been found that if an edge of the tip 14 and/or distal stem 12 is in engagement with the bony walls of the intramedullary canal 13, an incomplete cement mantle results and a higher incidence of loosening of the prosthesis occurs.

With reference to FIG. 6, it is seen that splines are cut into the tip 14 of the distal stem 12, with these splines being generally designated, in each case, by the reference numeral 20. Each spline 20 includes a distal end 21 which merges into a deeper proximal end 23 as best seen from the phantom lines in FIG. 6. The deeper proximal portions 23 of the splines 20 are provided for a purpose to be described in greater detail hereinafter. Each spline 20 terminates, proximally, at a proximal wall 25.

Figure 7:
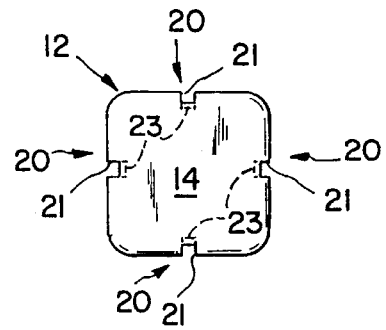
FIG. 7 shows an end view looking proximally at the tip of the distal stem.

FIG. 7 shows the four splines 20, each of which is orthogonal to the two respective adjacent splines 20 as best seen in FIG. 7.

Figure 8:
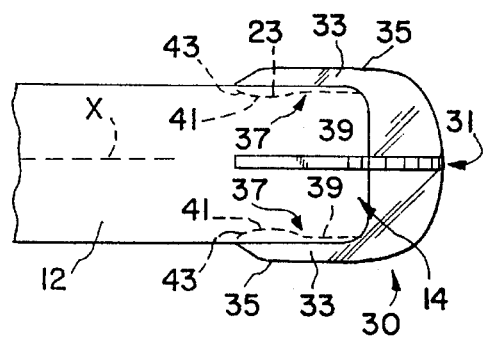
FIG. 8 shows a view similar to the view of FIG. 6 but with the inventive centralizer mounted over the tip of the distal stem.
Figure 9:
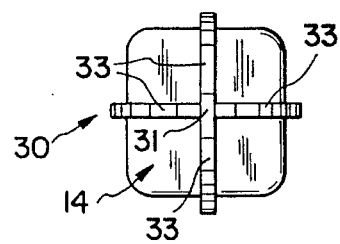
FIG. 9 shows a view similar to the view of FIG. 7 showing the centralizer installed over the tip of the distal stem.
Figure 10:
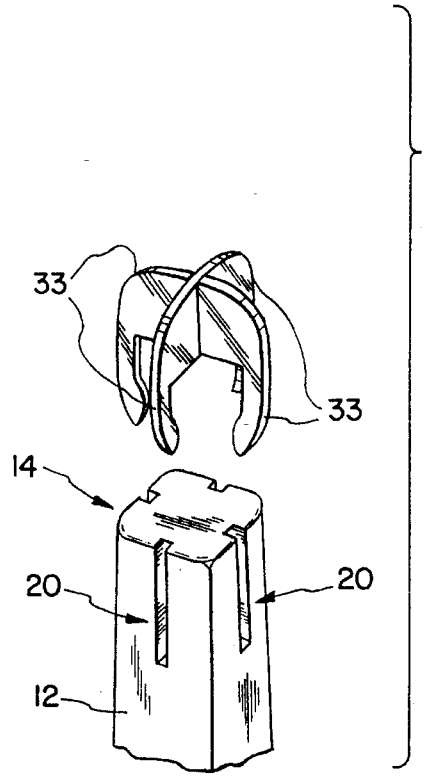
FIG. 10 shows an exploded isometric view of the inventive centralizer and the distal stem.

With reference to FIGS. 8, 9 and 10, the inventive centralizer 30 is seen to include a tip 31 as well as four legs 33 which radiate outwardly from the tip 31 and proximally as best seen in FIG. 8. Each leg 33 includes an outer surface 35 designed to engage the inner walls of the intramedullary canal 13 to centralize the prosthesis 15, proximal surfaces 43 corresponding to the surfaces 25 of the respective splines 20, radially thicker walls 41 designed to be complementary to the deeper proximal portions 23 of the splines 20 and relatively narrower portions 39 distal of the thicker portions 41 and designed to engage the relatively shallower portions 21 of the splines 20. As should be understood from FIG. 8, in particular, the centralizer 30 may be installed over the tip 14 of the distal stem 12 so that the thicker portions 41 of the legs 33 of the centralizer 30 enter the deeper portions 23 of the splines 20 to comprise locking means provided to lock the centralizer 30 in the mounted position shown, in particular, in FIGS. 4, 8 and 9. As best seen in FIG. 9, each of the legs 33 is extremely thin and extends parallel to the longitudinal axis X (FIG. 8) of the stem 12. In this way, when the stem 12 is inserted within the intramedullary canal 13 of the proximal femur 10, the legs 33 slide through the acrylic cement 26 quite easily and without creating any significant turbulence.

Thus, with the centralizer 30 installed as best seen in FIGS. 8 and 9, the surgeon may push the femoral prosthesis 15 distal stem 12 into the intramedullary canal 13 of the proximal femur 10 until the surfaces 35 of the legs 33 of the centralizer 30 engage the inner walls of the intramedullary canal 13 thereby centralizing the distal stem 12 and completing the installation of the femoral prosthesis 15. If, during the insertion process, the surgeon must pull the prosthesis 15 in the proximal direction, the interaction between the deeper portions 23 of the splines 20 and the relatively thicker portions 41 of the legs 33 of the centralizer 30 precludes disengagement of the centralizer 30 from the distal stem 12. In this way, the surgeon may insert the prosthesis 15 within the intramedullary canal 13 having the confidence of knowing that he or she may make minor positional adjustments of the distal stem 12 during the insertion process without fear that the centralizer 30 will become dislodged from the tip 14 of the distal stem.

In the preferred embodiment of the present invention, the inventive centralizer 30 is made of an acrylic plastic. The centralizer 30 may be made of a one-piece molded construction or, alternatively, the centralizer 30 may be made of two flat pieces assembled together at right angles to form the structure shown in the drawing figures and designated by the reference numeral 30.

In the preferred embodiment of the present invention, the splines 20 may be machined into the tip 14 of the distal stem 12 by a carbide slitting saw or any other suitable means.

Femoral prostheses are manufactured in up to six sizes having distal stem tips with thicknesses ranging from about ¼" to ½". As such, different sized centralizers 30 may be provided for each stem size. Alternatively, the splines 20 may be cut more deeply in the thicker stems to permit use of a single centralizer on any stem.

As such, an invention has been disclosed in terms of a preferred embodiment thereof which fulfills each and every one of the objects of the invention as set forth hereinabove and provides a new and useful distal stem centralizer for femoral prosthesis of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. In a prosthesis having a stem receivable within an intramedullary bone canal, said stem having a distal tip having a peripheral wall, and at least two elongated splines formed in said peripheral wall and extending in a proximal to distal direction, the improvement comprising a centralizer including:
   a) a distal centralizer tip;
   b) a plurality of legs extending proximally of said centralizer tip and in surrounding relation to said stem distal tip, at least some of said legs being received by respective splines to hold said centralizer on said stem distal tip; and
   c) locking means for securing said centralizer on said stem distal tip including a proximal portion of at least one of said splines being cut more deeply into said distal stem tip than a distal spline portion thereof.

2. The invention of claim 1, wherein said at least two splines comprise four splines with each spline being orthogonal with respect to two respective adjacent splines.

3. The invention of claim 2, wherein said plurality of legs comprise four legs.

4. The invention of claim 3, wherein said at least some of said legs comprises four legs.

5. The invention of claim 1, wherein a proximal portion of at least one of said legs which is adapted to enter said proximal portion of said at least one of said splines is radially thicker than a distal portion thereof, said proximal portion of said at least one of said legs being adapted to enter said proximal portion of said at least one of said splines to lock said centralizer on said distal stem tip.

6. The invention of claim 5, wherein said proximal portion of at least one of said splines comprises a proximal portion of each of said splines, and said proximal portion of at least one of said legs comprises a proximal portion of each of said legs.

7. The invention of claim 1, wherein said proximal portion of at least one of said splines comprises a proximal portion of each of said splines.

8. A distal stem centralizer for mounting on a distal stem of a femoral prosthesis, comprising:
   a) a distal centralizer tip; and
   b) a plurality of legs extending proximally of said centralizer tip, each of said legs having a proximal termination, said proximal terminations being spaced from one another, each leg having a thin distal portion adjacent said distal centralizer tip and at least one of said legs having a relatively thicker proximal portion, wherein the relatively thicker proximal portion has a section that extends further radially inward than an innermost section of the thin distal portion
   c) said centralizer being adapted to be mounted over a tip of a distal stem of a femoral prosthesis to centralize said distal stem within an intramedullary canal of a femur.

9. The invention of claim 8, wherein said plurality of legs comprises four legs.

10. The invention of claim 9, wherein each of said legs is orthogonal to two adjacent legs.

11. The invention of claim 9, wherein said centralizer is made of acrylic plastic.

12. The invention of claim 8, wherein said at least one of said legs comprises each of said legs.

* * * * *